United States Patent
Zeller

(10) Patent No.: US 10,962,620 B2
(45) Date of Patent: Mar. 30, 2021

(54) METHOD AND APPARATUS ACQUISITION OF MR MEASUREMENT DATA IN A BREATH-HOLD EXAMINATION

(71) Applicant: SIEMENS HEALTHCARE GMBH, Erlangen (DE)

(72) Inventor: Mario Zeller, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 734 days.

(21) Appl. No.: 15/659,765

(22) Filed: Jul. 26, 2017

(65) Prior Publication Data
US 2018/0031665 A1 Feb. 1, 2018

(30) Foreign Application Priority Data

Jul. 26, 2016 (DE) .................... 102016213632.1

(51) Int. Cl.
| | |
|---|---|
| *G01R 33/563* | (2006.01) |
| *A61B 5/00* | (2006.01) |
| *G01R 33/567* | (2006.01) |
| *A61B 5/055* | (2006.01) |
| *G01R 33/565* | (2006.01) |
| *A61B 5/08* | (2006.01) |

(52) U.S. Cl.
CPC ........ *G01R 33/56383* (2013.01); *A61B 5/055* (2013.01); *A61B 5/7207* (2013.01); *G01R 33/5676* (2013.01); *G01R 33/56509* (2013.01); *A61B 5/08* (2013.01); *A61B 5/082* (2013.01)

(58) Field of Classification Search
CPC .......... G01R 33/56383; G01R 33/5676; G01R 33/56509; A61B 5/055; A61B 5/7207; A61B 5/08; A61B 5/082
See application file for complete search history.

(56) References Cited

U.S. PATENT DOCUMENTS

| | | | |
|---|---|---|---|
| 2009/0112083 A1 | 4/2009 | Aulbach et al. | |
| 2012/0283548 A1 | 11/2012 | Greiser | |
| 2013/0211236 A1 | 8/2013 | Beck | |
| 2014/0024924 A1* | 1/2014 | Goto | ...................... A61B 5/113 600/413 |

\* cited by examiner

*Primary Examiner* — Bo Joseph Peng
(74) *Attorney, Agent, or Firm* — Schiff Hardin LLP

(57) ABSTRACT

In a method and magnetic resonance (MR) apparatus for acquisition of MR data from a patient in a breath-hold examination an instruction is provided to the patient to hold his/her breath, and the acquisition of MR measurement data is started. A breathing curve is recorded at least after the output of the instruction to the patient. A next-breath time is determined based on the recorded breathing curve. At least one final MR measurement data set is created based on the acquired MR measurement data, depending on the detected next-breath time. Image data are reconstructed from the at least one final MR measurement data set.

14 Claims, 4 Drawing Sheets

METHOD AND APPARATUS ACQUISITION OF MR MEASUREMENT DATA IN A BREATH-HOLD EXAMINATION

BACKGROUND OF THE INVENTION

Field of the Invention

The invention concerns a method for improving the acquisition of magnetic resonance (MR) measurement data in a breath-hold examination.

Description of the Prior Art

In many examinations using magnetic resonance technology, particularly in the thoracic and abdominal regions, motion artifacts occur due to the respiratory movement of the patient. One approach to reducing these artifacts is to perform the MR measurement during a time interval in which the patient holds his/her breath. For example, before an image recording sequence (raw data acquisition) is started, acoustic instructions are automatically issued to the patient, to hold his/her breath in the course of the expiration or the inspiration process. Immediately after this, the actual MR data recording process, also called the scanning process, takes place. Such breath-hold MR methods are performed using different pulse sequence types, for example TSE (turbo spin-echo) sequences, as well as HASTE (Half-Fourier Acquisition Single-shot Turbo spin-Echo) sequences and EPI (echo-planar imaging) sequences.

However, patients cannot always follow the given instructions to the extent desired. Normally, a patient is asked to hold his/her breath for a period of approximately 15 to 20 seconds. Many patients are unable to hold their breath for sufficiently long. Furthermore, patients often become restless toward the end of the breath-holding phase, which can even lead to movements that can interfere with the acquisition of data. This means that the last measurement data acquired are affected by the movement that occurred during that latter part of the acquisition. This can lead to an impairment of the image quality that can ultimately be achieved. In such cases, depending on the sequence used, only some of the image data generated are affected, e.g. when the measurement data are recorded in slices. In other cases, all the image data are compromised, e.g. in recordings that record only a defined area of k-space toward the end of the measurement, as may be the case in, for example, a VIBE (Volume Interpolated Breathhold Examination) sequence or a TSE sequence. Likewise, in a diffusion measurement, all the image data may be impaired by movements at the end of the recording of the measurement data, because in this case combined image data are obtained from different diffusion direction measurements, as a result of which motion effects in the last recorded diffusion direction measurements can impact adversely on the entire subsequent image.

SUMMARY OF THE INVENTION

An object of the invention is to provide a method, a magnetic resonance imaging apparatus, and a non-transitory, computer-readable storage medium that improve the quality of MR measurement data in a breath-hold examination, and in particular reduce losses of quality due to unwanted respiratory movements during the recording of the MR measurement data.

A method according to the invention for improving an acquisition of MR data from a patient in a breath-hold examination has the following steps. An instruction is given to the patient to hold his/her breath, and the acquisition of MR measurement data is then started. A breathing curve is recorded at least after the instruction to the patient. A next-breath time is detected based on the recorded breathing curve. At least one final MR measurement data set is created in a processor based on the acquired MR measurement data, depending on the detected next-breath time. Image data are reconstructed from the at least one final MR measurement data set, and the image data are made available in electronic form, as a data file.

In the method according to the invention an instruction is given, preferably as an automatic audio output via a speaker, to the patient to hold his/her breath. As an alternative to emitting the instruction to the patient automatically, a breath-hold instruction can also be triggered by operating personnel manually, e.g. via a switch. According to the invention, the breathing curve of the patient is recorded, preferably in real time. This can occur even before the breath-hold instruction is emitted. The recording of the breathing curve is started at least after the output of the instruction to the patient. If the recording of the breathing curve is started even before the output of the instruction to the patient to hold his or her breath, this has the additional advantage that the respiratory cycle of the patient can be used before the time of the intended breath-hold period of the patient, optionally as reference data and/or calibration data for the following detection step.

In each case, the breathing curve of the patient is recorded in time correlation with the acquisition of the MR measurement data. The acquisition of the MR measurement data is started as soon as it can be assumed that the patient has complied with the instruction to hold his/her breath. In an exemplary embodiment, the start of the acquisition of the measurement data can be triggered by the recorded breathing curve, when a breath-holding state has been detected. A breath-holding state is defined as the state of a patient in which he/she is not moving between two respiratory events and is holding his/her breath, or alternatively after expiring does not inspire, but stays at rest so that the thorax in particular does not move or moves only very little.

In each case, a next-breath time is detected, based on the recorded breathing curve. A next-breath time is defined as a time, as of which the patient leaves the breath-holding state, i.e. a time, as of which a movement takes place again due to resumed breathing. Based on this detected next-breath time, a final MR measurement data set is generated from the acquired MR measurement data. In this process, acquired MR measurement data that have been influenced by a respiratory movement can advantageously be detected, and measures can be taken to minimize or even to prevent completely any adverse influence of the acquired MR measurement data influenced by a respiratory movement on the final MR measurement data set. Ultimately, image data are reconstructed from the final MR measurement data set, which can be displayed and/or stored. The method according to the invention thus makes it possible, in spite of a failure by a patient to comply with actually specified breath-holding intervals, to insure an adequate quality of the MR measurement data on which an MR image is based. This increases the diagnostic value of the image data obtained. At the same time, repeat measurements that would otherwise be necessary if the quality of the image data were too poor are in this way avoided.

A breathing analysis processor has a command output unit for emitting an output instruction to the patient to hold his/her breath, a respiratory movement determination unit for recording a breathing curve of the patient in correlation with an acquisition of MR measurement data and a detection device for detecting a next-breath time in recorded breathing curves. The command output unit can be electrically connected, for example, to a speaker present in the area of the magnetic resonance scanner of a magnetic resonance imaging device so that instructions can be communicated acoustically to a patient located in the magnetic resonance scanner. The breathing commands are transmitted via an audio-communication unit to a patient located in the magnetic resonance scanner.

A magnetic resonance imaging apparatus according to the invention has as a scanner with a radio-frequency transmission system, a gradient system and a control computer configured to activate the radio-frequency transmission system and the gradient system to perform a desired acquisition of MR measurement data on the basis of a specified pulse sequence, as well as a breathing analysis processor. The breathing analysis processor can be, for example, part of the control computer of the magnetic resonance imaging apparatus according to the invention. It can also be only partially embodied in the control computer and can be distributed over multiple apparatus units. The breathing analysis processor also can be fitted as a supplementary unit or retrofit kit into a magnetic resonance imaging apparatus or integrated therein.

The basic components of the respiratory synchronization device according to the invention can be fashioned predominantly in the form of software components, in particular the command output unit, the respiratory movement determination unit and the detection device. In principle, these components can also in part, especially where particularly fast calculations are involved, be implemented in the form of software-supported hardware, for example FPGAs or the like. Likewise, the interfaces needed, for example where the transfer of data from other software components is involved, can be fashioned as software interfaces. They can also be fashioned as hardware-based interfaces that are controlled by suitable software.

A largely software-based implementation has the advantage that magnetic resonance imaging apparatuses or control computers of existing magnetic resonance imaging apparatuses already in use can easily be upgraded by a software update so as to function in the manner according to the invention.

The present invention also encompasses a non-transitory, computer-readable data storage medium encoded with programming instructions, which is loadable into a computer, or distributively loadable into a computer system, of a magnetic resonance imaging apparatus. The programming instructions, when executed by the computer or computer system, cause the computer or computer system to operate the magnetic resonance imaging apparatus in order to implement any or all of the embodiments of the inventive method described above.

DESCRIPTION OF THE PREFERRED EMBODIMENTS

Figure 1:
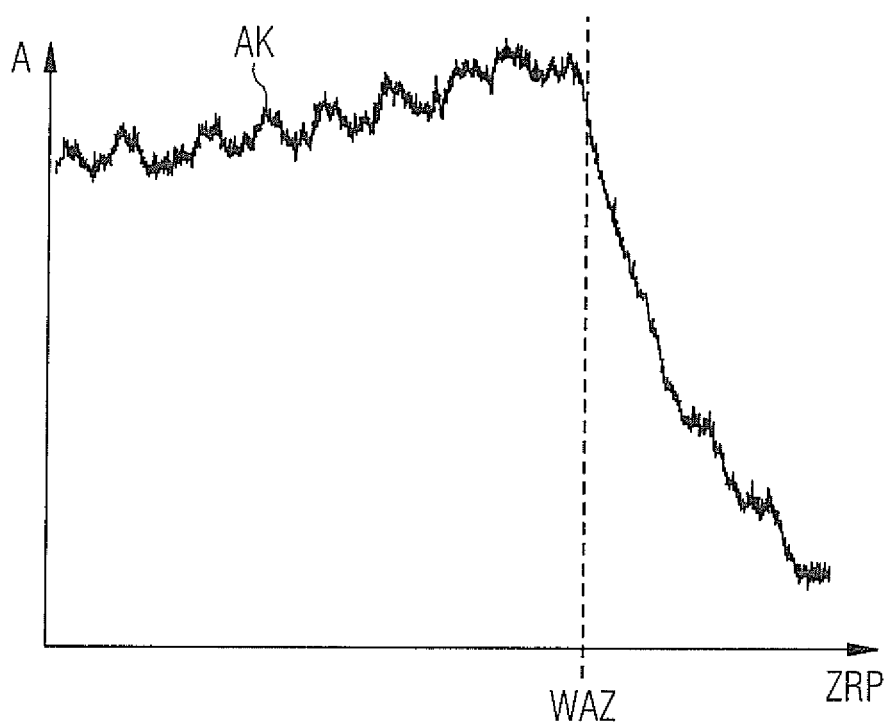
FIG. 1 is a diagram that illustrates a breathing curve depending on a scan time.

In FIG. 1 is an exemplary diagram of a breathing curve AK, which has been recorded for example with the use of an MR navigator sequence. In FIG. 1, respiratory state values A, e.g. in the form of phase values PHW of captured MR resonance signals of the MR navigator sequence, are recorded depending on the current repetition ZRP. The curve can be recorded e.g. through simple extraction of the phase portion of the MR signal of a body coil from the k-space center at each individual point in time. A smoother curve could be obtained for example through the use of surface coils and/or the application of a Fourier transformation and a signal-weighted summing of the image phases for each echo. In the respiratory curve shown in FIG. 1, respiration of a patient initially holding his/her breath can be seen. As of time WAZ, a renewed inspiration by the patient can be seen.

Figure 2:
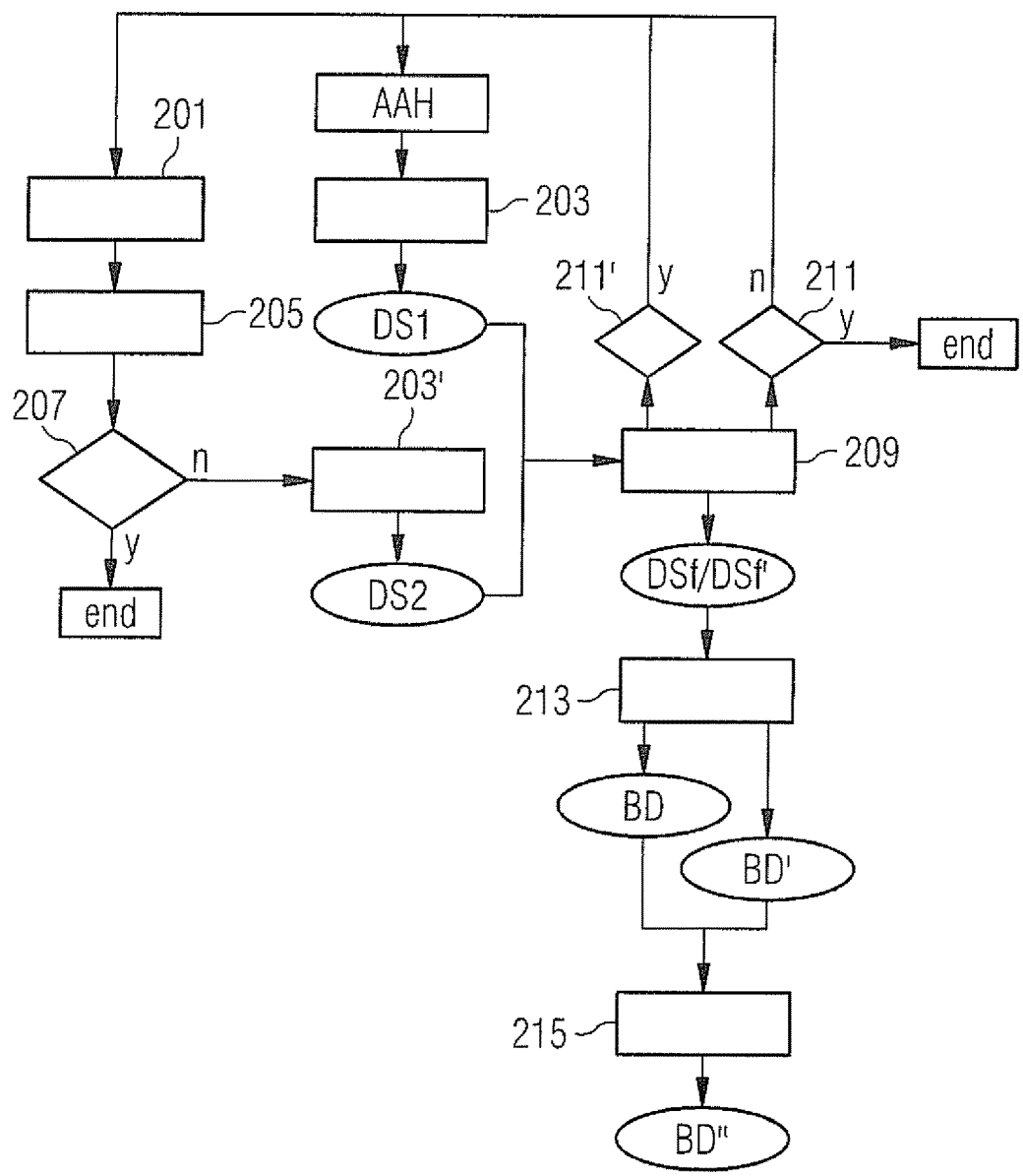
FIG. 2 is a flowchart of the method according to the invention.

FIG. 2 is a flowchart of the method according to the invention. Here, firstly, an instruction AAH is given to a patient, situated in a magnetic resonance scanner for an acquisition of MR data, to hold his/her breath.

If it can be assumed that the patient has followed the instruction AAH, so an acquisition of MR measurement data from the patient by execution of a preselected recording technique is started (block 203), and the acquired MR measurement data are stored in a data set DS1.

At least after the output of the instruction AAH to the patient, but possibly before that, recording of a breathing curve AK of the patient is started (block 201).

The breathing curve AK can be recorded with the use of an external device or with the use of an internal device.

Such an external device can be, for example, a respiratory belt or a sensor, preferably based on an electromagnetic reflection or a radar technology. Using such an external device, the respiratory movement of the patient can be recorded independently of the processes of the magnetic resonance imaging system, i.e. the monitoring process does not have to be integrated directly, for example as a pulse sequence, in the operating sequence of the magnetic resonance scanner.

Determination of the breathing pattern of the patient, preferably in real time, may also include monitoring the respiratory cycle of the patient with the use of an internal device. For example, this may be the execution of an MR navigator sequence, preferably having a series of non-phase-coded gradient echo subsequences. For the activation of an MR navigator sequence, a corresponding MR navigator sequence can be stored in the control computer or respiratory synchronization device that is used, or provided to the latter before the start of the actual MR imaging. Advantageously, no additional hardware, besides the magnetic resonance scanner already being used for MR imaging, is needed for respiratory cycle monitoring in this embodiment.

Alternatively or additionally, an MR detectable marker can be placed on the diaphragm and image-based tracking of the movement of the diaphragm can be carried out. This then also produces a breathing curve. Such a procedure is used e.g. within the context of the PACE method.

The breathing curve is recorded preferably by capturing MR signals in the center of k-space at a number of points in time and extracting the phase portion of the captured MR signal. In a signal coded in a spatial direction, the phase in the k-space center corresponds approximately to the phase averaged over all spatial domain points.

The breathing curve is determined preferably by capturing the MR signal using a body coil, applying a Fourier transformation and determining a signal-weighted sum of the signal phases for each readout time interval. In this way, a smoother breathing curve can be recorded, with which a more precise prediction of the start time of the breath-holding state of the patient can be predicted.

With the use of the Fourier transformation, the raw k-space data captured during the recording of the breathing curve are transformed into the spatial domain. In the spatial domain, the phase can be determined more stably. As already described, the k-space center phase corresponds to the averaging over the phases of all points in the spatial domain. If a determination is made in the spatial domain, a weighted averaging can be carried out. For example, points outside the body (associated with high level of noise) can be excluded and a weighting can be carried out, for example according to signal intensity.

For example, with an appropriately fashioned detection device of a breathing analysis processor, a next-breath time WAZ is detected on the basis of the recorded breathing curve AK (block 205).

Here, a next-breath time WAZ can be determined as the time at which a flat course of the breathing curve AK during a breath-holding phase of the patient is interrupted and a larger change occurs in the value of the breathing curve AK over time than is to be expected during the breath-holding phase, i.e. if a value of the breathing curve deviates relative to the last measured value of the breathing curve by more than a specified threshold value.

In particular, detection 201 of the next-breath time WAZ with the aid of an internal device may include at least one of the following method steps:

Comparison of time-dependent standard deviation values of the phase values of the captured MR signals, which were determined with a sliding time window, Comparison of temporal derivative values of the phase values of the captured MR signals with temporally earlier derivative values, Comparison of temporal derivative values of the phase values of the captured MR signals with a threshold value, Comparison of the absolute values of the phase values of the captured MR signals with a reference value.

A sliding time window in this context is to be understood as a time window that migrates temporally with the recording of the breathing curve, so that the current recording values in each case are also included in the calculation of the described variables. The first variant, which relates to the comparison of time-dependent standard deviation values of the phase values of the captured MR signals, which were determined with a sliding time window, can also be carried out without the prior recording of reference values, as the comparative values are obtained directly from the recorded breathing curve. The same applies to the second variant, in which temporal derivative values of the phase values of captured MR signal are compared with temporally earlier derivative values. In the third and fourth variants, threshold values or reference values can be determined for example through a learning phase upstream of the imaging process, wherein the breathing pattern of the patient concerned is examined by a prerecording of a breathing curve.

In an exemplary embodiment, the detection of a next-breath time can be assessed as a cancellation criterion for the acquisition of MR measurement data 203. If this is the case (Cancel? 207 "y") and if a next-breath time WAZ was detected, the acquisition of MR measurement data from the patient is cancelled from the detected next-breath time and no further MR measurement data is recorded ("end"). Otherwise (Cancel? 207 "n"), the acquisition of the MR measurement data continues (block 203').

Based on the acquired MR measurement data and depending on the detected next-breath time, a final MR measurement data set DSf is created (block 209) from which image data BD can be reconstructed (block 213). If the acquisition of the MR measurement data was cancelled as soon as a next-breath time was detected (Cancel? 207 "y"), the final MR measurement data set comprises the MR measurement data acquired before detection of the next-breath time, i.e. the MR measurement data of the first data set DS1.

If the MR measurement data were recorded using an acquisition technique in which certain areas, for example slices, or k-space lines or k-space partitions in k-space, are recorded multiple times, the image data BD can be reconstructed in block 213 solely from the acquired MR measurement data of the first data set DS1. This is the case, for example, in an EPI diffusion acquisition technique, in which various diffusion values, called b-values, are recorded multiple times in order to be able to carry out averaging. In this case, e.g. MR measurement data from repetitions of the actually planned data acquisition, which are then missing, can be omitted and the image data BD reconstructed solely from the MR measurement data of the first data set DS1, which was available by then, are recorded repeatedly and averaged. This omission of some (a few) repetitions in the averaging of the MR measurement data of the first data set DS1 will generally speaking still lead to higher-quality image data BD than any use of MR measurement data influenced by the resuming respiratory movement of the patient.

If the MR measurement data were recorded using an acquisition technique in which certain areas, such as slices, or k-space lines or k-space partitions, are each recorded only once (as is the case, for example, with VIBE or TSE recording techniques) and if in the acquisition of the MR measurement data multiple receiver coils are used, missing MR measurement data due to cancellation of the acquisition of the MR measurement data (Cancel? 207 "y") can possibly be supplemented using methods for parallel acquisition techniques. This takes place based on the acquired MR measurement data of the first data set DS1, in order to supplement or complete the final MR measurement data set DSf (e.g. in block 209), or to supplement or complete the image data BD reconstructed on the basis of the first data set DS1 (e.g. in block 213).

For this purpose, reconstruction kernels of a parallel acquisition technique used, such as e.g. GRAPPA ("GeneRalized Autocalibrating Partial Parallel Acquisition") or SENSE ("SENSitivity Encoding"), can be calibrated in accordance with the acquired MR measurement data present in the first data set DS1 in order to reconstruct missing MR measurement data with an adapted acceleration factor. If a parallel acquisition technique is already being used, the missing MR measurement data can be reconstructed from the acquired MR measurement data of the first data set DS1 using a correspondingly higher acceleration factor. The MR measurement data in the first data set DS1 acquired before detection of the next-breath time WAZ contain no interfering influences due to the resuming respiratory movement and are thus suitable as a basis for a reconstruction kernel used. Since only the missing MR measurement data are reconstructed, or reconstruction is performed with a higher acceleration factor, the finally resulting image data can nonetheless be expected to be on the whole of a better quality than if MR measurement data corrupted by a resuming respiratory movement were used. Here, depending on how the missing MR measurement data are arranged in k-space (e.g. the pattern of missing k-space lines), multiple different reconstruction kernels can be created and applied for different missing MR measurement data.

If the acquisition of MR measurement data was not cancelled as soon as a next-breath time was detected (Cancel? 207 "n"), the acquisition of MR measurement data continues (block 203'). The MR measurement data acquired after the next-breath time WAZ can now be classified and stored in a second MR measurement data set DS2. The acquired MR measurement data are thus classified depending on the detected next-breath time in a first data set DS1 and in a second data set DS2, the first data set DS1 containing MR measurement data, which was acquired before the next-breath time WAZ, and the second data set DS2 containing MR measurement data, which was acquired after the next-breath time WAZ.

In this case as well, the final MR measurement data set DSf can, as in the cases already described above, be created only on the basis of the MR measurement data from the first data set DS1 (block 209).

However, it is also possible to create the final MR measurement data set DSf on the basis of MR measurement data of the first data set DS1 and the second data set DS2 (block 209).

In a simple exemplary embodiment, the MR measurement data of the first data set DS1 and the second data set DS2 can be grouped together to form the final MR measurement data set DSf. If MR measurement data that are important, e.g. for contrast, are missing from the MR measurement data of the first data set DS1, it can be useful also to incorporate in the reconstruction the MR measurement data of the second data set DS2 compromised by the resuming respiratory movement of the patient.

Here, as described above, image data can also initially be reconstructed only from a final MR measurement data set DSf, which was created only on the basis of the first data set DS1, and which consequently exhibit no influences due to the resuming respiratory movement. In addition, further image data BD' can be reconstructed from a further final MR measurement data set that was created on the basis of the MR measurement data from both the first data set DS1 and the second data set DS2, which consequently exhibit interfering influences due to the resuming respiratory movement. These sets of image data BD and BD' can now be processed together to form mixed image data BD", e.g. by being averaged, optionally using a specified weighting which takes account of the degree of interfering influences due to the resuming respiratory movement.

Thus, from at least two final MR measurement data sets, in each case a set of image data BD, BD' can be reconstructed, which is processed to form a set of mixed image data BD".

In a further exemplary embodiment, a final MR measurement data set DSf can also be created on the basis of only selected MR measurement data of the first and second data sets DS1 and DS2. Here, particularly from the MR measurement data of the second data set DS2, which is influenced by the resuming respiratory movement, only the MR measurement data that are needed for a subsequent reconstruction 213 can be selected, while other MR measurement data of the second data set DS2 cannot be taken into consideration for the final MR measurement data set. This could be the case, e.g. in a diffusion measurement, where not even at least one b-value is contained in the MR measurement data of the first data set DS1 but was recorded in the course of the further acquisition of MR measurement data, and is therefore present only in the second data set DS2.

It is also possible to iteratively determine a final MR measurement data set DSf, DSf from the first data set with the use of selected MR measurement data of the second data set. Here, the movement-influenced MR measurement data of the second data set DS2 are used as training data for the iterative reconstruction and/or for checking the consistency of the reconstruction. As an iterative method of this kind, e.g. iGRAPPA ("iterative GRAPPA") or SPIRiT ("(iterative self-consistent parallel imaging reconstruction") can be used.

In a further exemplary embodiment, a check can be made after detection of the next-breath time WAZ, e.g. in the creation of the final MR measurement data set in block 209, as to whether the MR measurement data acquired by the time of the next-breath time WAZ are already complete (query 211). If the data are already complete (query 211 "y"), the acquisition of MR measurement data can be terminated ("end"). If the data are not complete (query 211 "n"), an instruction AAH can be given to the patient again to hold his/her breath. In the renewed acquisition of MR measurement data 203 that now follows, the missing MR measurement data can now be acquired. Advantageously, only the missing MR measurement data are acquired in the renewed acquisition of MR measurement data. The MR measurement data recorded little by little in this way, in each case during a breath-holding phase of the patient, can be stored in a final MR measurement data set DSf until the latter is complete and image data can be reconstructed therefrom.

"Complete" is understood herein as meaning that the MR measurement data previously acquired before a detected next-breath time WAZ, possibly using a method as described above for adding missing MR measurement data, is already sufficient to reconstruct the desired image data.

Such a procedure is to be recommended e.g. where the MR measurement data are recorded in sections, e.g. in slices, as is the case, for example when recording MR measurement data using a HASTE sequence. If, by a detected next-breath time WAZ, all the slices have not yet been measured, the missing layers can be acquired after the renewed instruction AAH to the patient to hold his/her breath until all the required layers have been measured. As a result, only MR measurement data that are not influenced by a respiratory movement of the patient are used for the reconstruction of image data.

In addition, or as an alternative, to the measures already mentioned, the breath-holding capacity of the patient can be determined, e.g. as part of the creation of the final MR measurement data set in block 209, after detection of the next-breath time. This can be done, for example, simply by determining the time that has elapsed between the output of the instruction AAH to the patient to hold his/her breath and the detection of the next-breath time WAZ. If the determined breath-holding capacity of the patient deviates from a breath-holding duration with which the process of acquisition of MR measurement data was planned, to such an extent that difficulties with the measurement procedure can be expected (query 211' "y"), the entire measurement can be started with parameters adapted to the determined breath-holding capacity of the patient, i.e. a new instruction AAH is given to the patient to hold his/her breath and the acquisition of the MR measurement data is performed with adapted parameters and a final MR measurement data set is created from the acquired MR measurement data. Depending on the sequence to be performed, parameters to be adapted here may be: a repetition time TR, a number of breath-holding states needed in total, a number of required averagings, a recording matrix size, or a parallel acceleration factor.

Such an approach is particularly useful where the measurement has been planned from the outset such that multiple breath-holding phases are provided for the complete acquisition of the desired MR measurement data. Such an adaptation of the measurement procedure to the actual breath-holding capacity of the patient not only increases the level of comfort for the patient, but also can shorten the measurement overall, because a lesser amount of recorded MR measurement data is likely to be corrupted by respiratory movements, and consequently additional (re)measurements that might otherwise be necessary are avoided.

Here, the determination of the breath-holding capacity and the adaptation of the parameters for the measurement can also be carried out starting the acquisition of MR measurement data. To this end, the breath-holding capacity can be determined in advance by giving an instruction AAH to the patient to hold his/her breath, and detecting the following next-breath time WAZ. In this way, measurement time for the acquisition of MR measurement data can be saved, and the SAR load (SAR: specific absorption rate) on the patient can be reduced.

In an exemplary embodiment, a user can reconstruct image data BD and BD' in different ways, compare the resulting different image data BD and BD' and choose the better result for him/her. If the user is not yet satisfied with the image data obtained, he/she can also choose a further reconstruction method in order to generate still further image data BD'.

Figure 3:
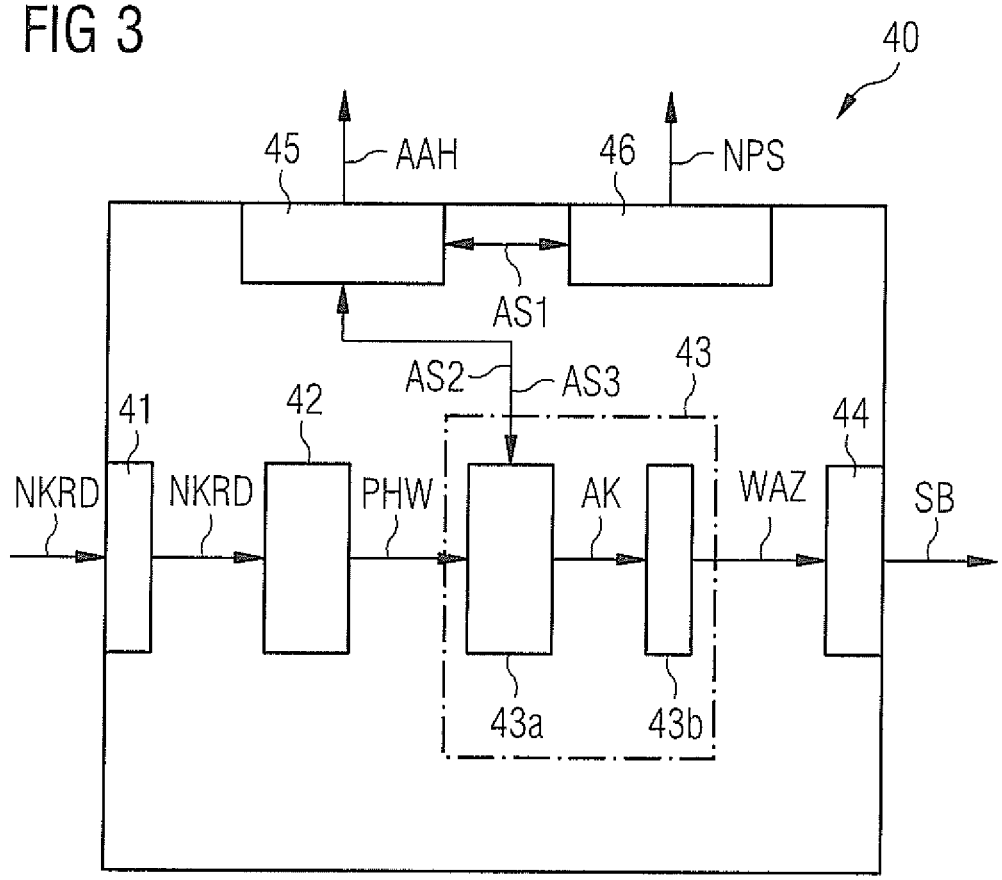
FIG. 3 is a block diagram that illustrates a breathing analysis processor according to an exemplary embodiment of the invention.

FIG. 3 shows schematically a breathing analysis processor 40. The breathing analysis processor 40 can be, for example, part of a control computer of a magnetic resonance imaging system (see FIG. 4). The breathing analysis processor 40 has a raw-data-capture unit 41, which receives raw data, in this exemplary embodiment navigator-k-space data NKRD that have been recorded in the course of a navigator acquisition. The raw data NKRD are transmitted to a phase-value determination unit 42, which extracts phase values PHW from the raw data NKRD. The phase values PHW are then transferred to a respiratory movement determination unit 43. The respiratory movement determination unit 43 has a breathing curve recording unit 43a, which is configured to record, based on the received phase values PHW, in real time a breathing curve AK of a patient to be examined. The respiratory movement determination unit 43 furthermore has a detection device 43b, which determines, on the basis of the captured breathing curve AK, the next-breath time WAZ, at which the patient starts to continue breathing again after a breath-holding phase. Based on this time information WAZ, a trigger signal SB can be transmitted via a signaling device 44 to a data storage unit (not shown), which stores acquired MR measurement data in accordance with a received trigger signal in different data sets. The breathing analysis processor 40 furthermore has a command output unit 45 for automatically emitting an instruction AAH as an output to the patient O to hold his/her breath. The command output unit 45 can be connected to the respiratory movement determination unit 43 in order to trigger a start of operation of the respiratory movement determination unit 43, for example by transmitting a trigger signal AS2 after a breath-hold command has been issued. The breathing analysis processor 40 can furthermore have a navigator-sequence generating unit 46, by which a navigator pulse sequence NPS is generated in order to record navigator k-space data NKRD of the respiratory movement of the patient. The navigator-sequence generating unit 46 can transmit a trigger signal AS1 to the command output unit 45 in order to prompt the command output unit 45 to emit a breath-hold command AAH automatically, in this case, after the navigator pulse sequence NPS has been activated. Other times for the activation of the breath-hold command AAH are also possible. For example, the breath-hold command can also be emitted chronologically before the navigator pulse sequence NPS is activated.

Figure 4:
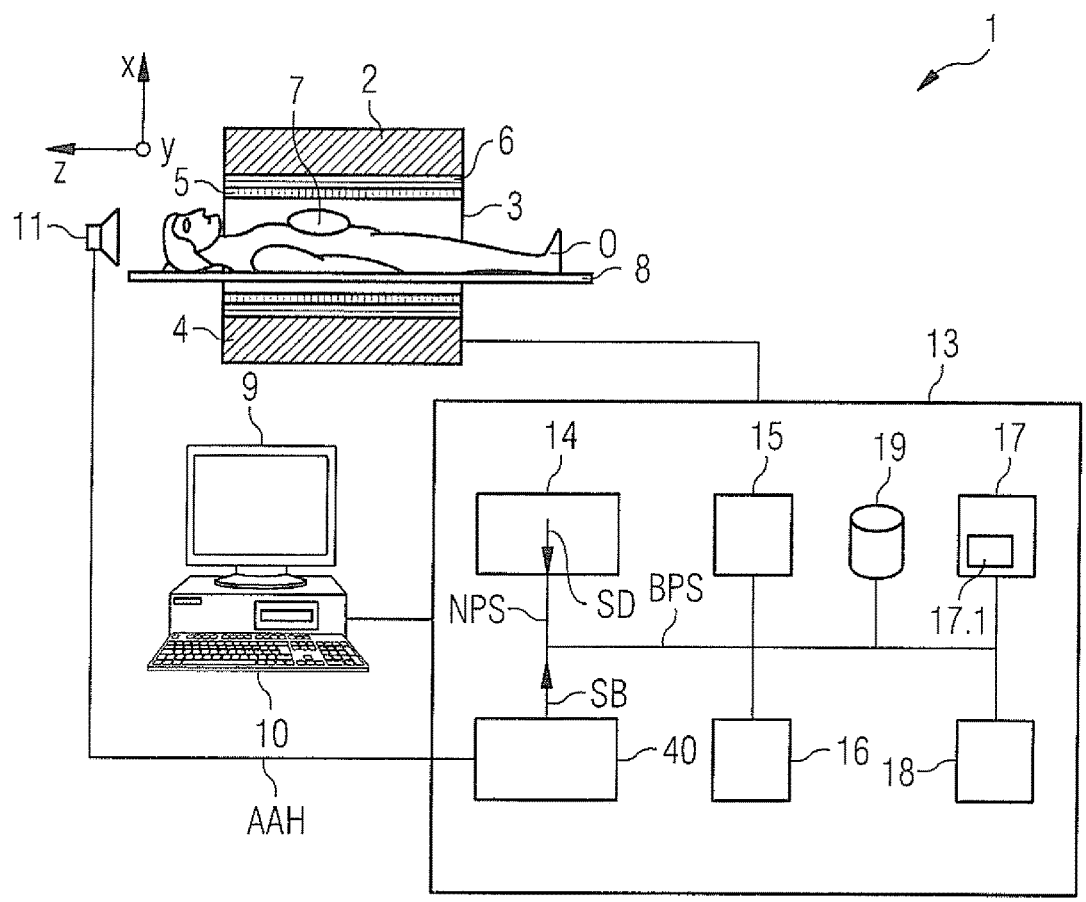
FIG. 4 shows a magnetic resonance imaging apparatus according to an exemplary embodiment of the invention.

FIG. 4 is a schematic illustration of a magnetic resonance (MR) imaging apparatus 1 according to the invention. The MR system has the actual magnetic resonance scanner 2 with an examination space 3 or patient tunnel, into which an examination object O, here a patient or test person, can be moved on a bed 8. The examination object, for example a particular organ, is situated in the object O.

The magnetic resonance scanner 2 is fitted in the customary manner with a basic field magnet system 4, a gradient system 6 and an RF transmitting antenna system 5 and an RF receiving antenna system 7. In the exemplary embodiment, the RF transmitting antenna system 5 is a whole-body coil integrated in the magnetic resonance scanner 2, whereas the RF receiving antenna system 7 is formed by local coils that can be arranged on the patient or test person (symbolized in FIG. 4 only by a single local coil). In principle, however, the whole-body coil can also be used as the RF receiving antenna system and the local coils as the RF transmitting antenna system, provided these coils can each be switched to different operating modes.

The MR system 1 furthermore has a central control computer 13, which is configured to control the MR system 1. This central control computer 13 has a sequence controller 14 for pulse sequence control. This is used to control the sequence of radio-frequency pulses (RF pulses) and gradient pulses, depending on a chosen imaging sequence. Such an imaging sequence can be specified, for example, within a measurement or control protocol. Normally, different control protocols for different measurements are stored in a memory 19 and can be selected by an operator (and, if required, optionally modified) and then used for carrying out the measurement.

For radiating the individual RF pulses, the central control computer 13 has a radio-frequency transmitting device 15, which generates the RF pulses, amplifies them and feeds them via a suitable interface (not shown) into the RF transmitting antenna system 5. For controlling the gradient coils of the gradient system 6, the control computer 13 has a gradient system interface 16. The sequence controller 14 communicates in a suitable manner, e.g. by emitting sequence control data SD, with the radio-frequency transmitting device 15 and the gradient system interface 16 in order to emit the pulse sequences. The control computer 13 also has a radio-frequency receiving device 17, (also communicating in a suitable manner with the sequence control unit 14) for acquiring magnetic resonance signals, i.e. MR measurement data (also called raw data) received from the RF transmitting antenna system 7, and for storage with a data storage unit 17.1 e.g. in the memory 19. A reconstruction unit 18 imports the acquired MR measurement data and reconstructs MR image data therefrom. The image data can then be filed for example in the memory 19 and/or, in the case of navigator data, further processed in a breathing analysis device 40 according to the invention, in order to control the storage of acquired MR measurement data by the data storage unit 17.1 and if necessary a renewed start of an acquisition of MR measurement data. Furthermore, the breathing analysis processor 40 also has a connection to an audio-communication unit 11 on the magnetic resonance scanner 2 in order to transmit breath-holding instructions AAH to the patient O.

The central control computer 13 can be operated via a terminal with an input unit 10 and a display unit 9, via which the entire MR system 1 can thus also be operated by an operator. MR images can also be displayed on the display unit 9, and with the input unit 10, optionally in combination with the display unit 9, measurements can be planned and started, and suitable control protocols with suitable measurement sequences, as explained above, are selected and optionally modified.

The MR system 1 according to the invention, and in particular the control computer 13, can also have further components, not shown in detail here, that are usually present on such devices, such as a network interface in order to connect the entire system to a network and to be able to exchange raw data and/or image data, and parameter cards but also other data such as, for example, patient-related data or control protocols.

The manner by which raw data are acquired by the radiation of RF pulses and the generation of gradient fields, and MR images reconstructed therefrom are known to those skilled in the art, and need not be explained in detail herein. Likewise, diverse measurement sequences, such as EPI measurement sequences or measurement sequences for generating diffusion-weighted images, are known to those skilled in the art.

The methods and devices described above are only exemplary embodiments of the invention, and invention can be varied by a person skilled in the art without departing from the scope of the invention. Thus, the method for improving the acquisition of MR data from a patient O in a breath-hold examination and the breathing analysis processor 40 were explained primarily using a recording of a breathing curve AK with the use of a navigator pulse sequence. The invention is not restricted to this application, but the recording of a breathing curve can also be implemented with the use of an external detector.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for acquiring magnetic resonance (MR) data from a patient in a breath-hold examination, comprising:
   providing an instruction to a patient situated in an MR data acquisition scanner to hold his or her breath;
   starting, via a processor, operation of said MR data acquisition scanner to acquire MR measurement data from the patient;
   acquiring a breathing curve representing breathing of the patient at least after providing said instruction to the patient;
   providing said breathing curve to said processor and, via said processor, detecting a next-breath time based on said breathing curve;
   via said processor, generating at least one final MR measurement data set based on measurement data selected from the acquired MR measurement data depending on the detected next-breath time; and
   via said processor, reconstructing image data from said at least one final MR measurement data set, and making the image data available in electronic form, as a data file, from said processor.

2. A method as claimed in claim 1, comprising:
   via said processor, operating the MR data acquisition scanner to stop a current acquisition of said MR measurement data upon detecting the next-breath time, and using, as said final MR measurement data set, a previous set of said MR measurement data that was acquired before detecting said next-breath time and stopping the acquisition of said MR measurement data.

3. A method as claimed in claim 2, comprising:
   via said processor, generating MR measurement data or image data, which are absent due to stopping of the acquisition of said MR measurement data, using a parallel acquisition algorithm.

4. A method as claimed in claim 1, comprising:
   via said processor, subdividing the acquired MR measurement data, dependent on the detected next-breath time, into a first data set and a second data set, said first data set containing MR measurement data acquired before the next-breath time, and the second data set containing MR measurement data acquired after said next-breath time.

5. A method as claimed in claim 4, comprising
   via said processor, creating said final MR measurement data set using only MR measurement data from said first data set.

6. A method as claimed in claim 4, comprising:
   creating said final MR measurement data set from MR measurement data in each of said first data set and said second data set.

7. A method as claimed in claim 6, comprising:
   creating said final MR measurement data set using only selected MR measurement data from said first and second data sets.

8. A method as claimed in claim 6, comprising:
   creating said final MR measurement data set iteratively from said first data set using selected MR measurement data from said second data set.

9. A method as claimed in claim 1, comprising:
   via said processor, after detecting said next-breath time, checking whether the MR measurement data acquired preceding said next-breath time are complete; and, if said MR measurement data acquired preceding said next-breath time are not complete, repeating the instruction to the patient to hold his or her breath, and thereafter operating the MR data acquisition scanner to acquire additional MR measurement data to complete said MR measurement data acquired preceding said next-breath time.

10. A method as claimed in claim 1, comprising:
    via said processor, after detecting said next-breath time, determining a breath-holding capacity of the patient; and
    repeating, with parameters adjusted to the determined breath-holding capacity, the acts of providing some instruction to the patient, starting the acquisition of said MR measurement data, recording said breathing curve, detecting said next-breath time, and creating said at least one final MR measurement data set.

11. A method as claimed in claim 1, comprising:
via said processor, reconstructing a first set of image data and a second set of image data, respectively, from each of at least two final MR measurement data sets; and
via said processor, processing the first set of image data and the second set of image data to generate a single set of image data.

12. A breathing analysis computer, comprising:
a command output interface configured to emit an instruction to a patient to hold his or her breath;
a respiratory movement determination processor configured to record a breathing curve of the patient correlated with acquisition of MR measurement data; and
a detection processor configured to detect a next-breath time in the recorded breathing curve,
wherein the detection of the next-breath time enables the generation of at least one final MR measurement data set based on measurement data selected from MR measurement data acquired via the acquisition of the MR measurement data, the measurement data being selected from the MR measurement data depending on the detected next-breath time.

13. A magnetic resonance (MR) imaging apparatus comprising:
an MR data acquisition scanner;
a processor configured to provide an instruction to a patient situated in the MR data acquisition scanner to hold his or her breath, said processor being configured to:
start operation of said MR data acquisition scanner to acquire MR measurement data from the patient;
acquire a breathing curve representing breathing of the patient at least after providing said instruction to the patient;
detect a next-breath time based on said breathing curve;
generate at least one final MR measurement data set based on measurement data selected from the acquired MR measurement data depending on the detected next-breath time; and
reconstruct image data from said at least one final MR measurement data set, and to make the image data available in electronic form, as a data file, from said processor.

14. A non-transitory, computer-readable data storage medium encoded with programming instructions, said storage medium being loaded into a computer system of a magnetic resonance (MR) apparatus comprising an MR data acquisition scanner, said programming instructions causing said computer system to:
provide an instruction to a patient situated in the MR data acquisition scanner to hold his or her breath;
start operation of said MR data acquisition scanner to acquire MR measurement data from the patient;
acquire a breathing curve representing breathing of the patient at least after providing said instruction to the patient;
detect a next-breath time based on said breathing curve;
generate at least one final MR measurement data set based on measurement data selected from the acquired MR measurement data depending on the detected next-breath time; and
reconstruct image data from said at least one final MR measurement data set, and make the image data available in electronic form, as a data file, from said processor.

* * * * *